United States Patent
Hatcher, Jr. et al.

(10) Patent No.: US 9,255,526 B2
(45) Date of Patent: Feb. 9, 2016

(54) SYSTEM AND METHOD FOR ON LINE MONITORING WITHIN A GAS TURBINE COMBUSTOR SECTION

(71) Applicants: Clifford Hatcher, Jr., Orlando, FL (US); Richard Hatley, Morristown, NJ (US); Yakup Genc, Dayton, NJ (US); Forrest R. Ruhge, Orlando, FL (US)

(72) Inventors: Clifford Hatcher, Jr., Orlando, FL (US); Richard Hatley, Morristown, NJ (US); Yakup Genc, Dayton, NJ (US); Forrest R. Ruhge, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 489 days.

(21) Appl. No.: 13/856,673

(22) Filed: Apr. 4, 2013

(65) Prior Publication Data
US 2014/0053568 A1 Feb. 27, 2014

Related U.S. Application Data

(60) Provisional application No. 61/692,416, filed on Aug. 23, 2012.

(51) Int. Cl.
| | | |
|---|---|---|
| *G01J 3/00* | (2006.01) | |
| *F02C 9/00* | (2006.01) | |
| *G01M 11/08* | (2006.01) | |
| *G01M 15/14* | (2006.01) | |
| *G01N 21/88* | (2006.01) | |
| *F02C 7/00* | (2006.01) | |
| *G01N 25/72* | (2006.01) | |
| *G01J 5/00* | (2006.01) | |
| *G01H 9/00* | (2006.01) | |

(Continued)

(52) U.S. Cl.
CPC ... *F02C 9/00* (2013.01); *F02C 7/00* (2013.01); *G01M 11/081* (2013.01); *G01M 15/14* (2013.01); *G01N 21/8851* (2013.01); *G01N 25/72* (2013.01); *F05D 2260/80* (2013.01); *G01H 9/00* (2013.01); *G01J 5/0088* (2013.01); *G01J 2005/0077* (2013.01); *G01N 21/8806* (2013.01); *G01N 21/954* (2013.01); *G01N 21/9515* (2013.01); *G01N 2021/8893* (2013.01)

(58) Field of Classification Search
CPC ... G01J 5/0088; G01J 2005/0077; F02C 7/00; G01N 25/72; G01N 21/954; G01N 2021/8893; G01M 11/081
See application file for complete search history.

(56) References Cited

U.S. PATENT DOCUMENTS

| | | |
|---|---|---|
| 3,899,882 A | 8/1975 | Parker |
| 4,557,106 A | 12/1985 | Ffowcs Williams et al. |

(Continued)

FOREIGN PATENT DOCUMENTS

WO 2009061586 A2 5/2009

*Primary Examiner* — Gregory J Toatley
*Assistant Examiner* — Maurice Smith

(57) ABSTRACT

An on-line optical inspection and monitoring system is externally mounted to existing man way service access within the combustor housing. A replacement man way cover having an optical window is mounted to the combustor housing. One or more optical cameras are oriented so that the camera field of view (FOV) is directed through the man way cover optical window. The camera FOV is moved to plural positions within the combustion section, such as under control of an automated motion control system, and images are captured. Multiple images are combined to form a composite image, which may include an image of an entire transition within the combustion section. Visual images and/or infrared (IR) thermal images may be captured. Thermal image information is correlated with component temperature. Image information is utilized to determine vibration characteristics of the imaged components.

21 Claims, 6 Drawing Sheets

(51) Int. Cl.
*G01N 21/95* (2006.01)
*G01N 21/954* (2006.01)

(56) References Cited

U.S. PATENT DOCUMENTS

| | | | |
|---|---|---|---|
| 4,751,571 A * | 6/1988 | Lillquist | G01J 5/48 250/330 |
| 5,242,224 A | 9/1993 | Yoshioka et al. | |
| 5,544,478 A | 8/1996 | Shu et al. | |
| 5,694,202 A | 12/1997 | Mladjan et al. | |
| 5,828,797 A | 10/1998 | Minott et al. | |
| 6,354,071 B2 | 3/2002 | Tegel et al. | |
| 6,461,144 B1 | 10/2002 | Gutmark et al. | |
| 7,533,572 B2 | 5/2009 | Twerdochlib | |
| 2004/0159790 A1 * | 8/2004 | Thompson | G01N 25/72 250/341.6 |
| 2005/0199832 A1 | 9/2005 | Twerdochlib | |
| 2006/0075755 A1 | 4/2006 | Haertel et al. | |
| 2006/0091310 A1 * | 5/2006 | Furry | G01J 5/061 250/330 |
| 2007/0296964 A1 | 12/2007 | Nishimura et al. | |
| 2009/0302242 A1 | 12/2009 | Papadopoulos | |
| 2010/0020310 A1 * | 1/2010 | Merklein | F23N 5/082 356/51 |
| 2011/0062339 A1 * | 3/2011 | Ruhge | G01N 25/72 250/340 |
| 2013/0194412 A1 | 8/2013 | Hatcher et al. | |
| 2013/0194413 A1 | 8/2013 | Hatcher et al. | |

* cited by examiner

SYSTEM AND METHOD FOR ON LINE MONITORING WITHIN A GAS TURBINE COMBUSTOR SECTION

CROSS-REFERENCE TO RELATED APPLICATIONS

This application claims the benefit of United States provisional patent application entitled "On-Line Monitoring Of The Cold Side Of Gas Turbine Transitions" filed Aug. 23, 2012 and assigned Ser. No. 61/692,416, which is incorporated by reference herein.

This application also incorporates in its entirety by reference herein commonly owned co-pending United States patent application entitled "System For Remote Vibration Detection On Combustor Basket And Transition In Gas Turbines", filed Aug. 22, 2012 and assigned Ser. No. 13/591,635.

BACKGROUND OF THE INVENTION

1. Field of the Invention

The invention relates to on-line optical monitoring within a gas turbine combustor section, and more particularly to an optical system and inspection method that mounts one or more optical cameras outside a combustor man way service access on a man way cover having an optical window. The external camera field of view is oriented through the optical window and captures images of combustion section internal components, such as transitions. Image information is used to inspect, monitor and/or map one or more of observable structural condition, vibration and/or temperature distributions within the combustor section.

2. Description of the Prior Art

Monitoring of steady state and transient temperature and/or vibration characteristics within a gas turbine combustor section, and especially the transition components, are desirable tools for turbine design, validation and operation. Those components are susceptible to induced temperature and vibration transient excitations caused by combustion gas dynamics. Given the efficiency and emissions criteria, the operation of gas turbines requires a balancing of design and operational approaches to maintain efficiency, meet emission standards, and avoid vibrational and/or thermal damage due to undesired combustion dynamics characteristics. Thus during gas turbine engine design and subsequent field operation it is beneficial to monitor either or both of combustion thermal and vibration characteristics, whether transient or steady-state, that may damage combustor components such as transitions.

In particular, on-line vibration and thermal monitoring of combustor transitions with instruments is difficult given the local pressure and temperature conditions within a combustor. Known combustion characteristic monitoring instrumentation include single thermocouples or thermocouple arrays oriented within the combustor, that associate temperature and/or changes in temperature with combustion characteristics. However, even an array of thermocouples only provides localized temperature information at discrete locations that may not necessarily be extrapolated to determine temperature conditions in other combustor locations that do not have thermocouples. On-line monitoring instruments embedded within the combustor section are subject to greater temperature and pressure environments than ambient conditions outside the combustor section. Embedded instruments are susceptible to damage from hot pressurized combustion gasses, reducing their potential service reliability, and lifetime. Failed embedded instruments require engine shutdown—hence service interruption—to facilitate their removal or replacement.

Other known gas turbine combustor section temperature and vibration monitoring instrumentation determine local characteristics at monitored sites. However, as with thermocouple arrays, the localized information obtained at discrete locations that may not necessarily be extrapolated to determine similar information in other combustor locations. Exemplary known localized temperature and vibration monitoring instrumentation sensors include: embedded pressure transducers (e.g., piezo-electric transducers); embedded and externally mounted accelerometers; and optical systems that associate flame luminescence with combustion thermoacoustic vibration characteristics. The previously cited commonly owned co-pending United States patent application entitled "System For Remote Vibration Detection On Combustor Basket And Transition In Gas Turbines", filed Aug. 22, 2012 and assigned Ser. No. 13/591,635 is directed to externally mounted photonic transmitters and receivers that reflect photons off combustor section internal surfaces and correlate the reflections with internal vibration characteristics. The externally mounted transmitters and receivers pass photons through optical windows affixed to inspection ports and the like. Other laser-optical sensors employing backscatter, diffraction or phase-Doppler principles have been proposed for monitoring cooling water injection content and droplet distribution within the combustor.

Thus, a need exists for an on-line gas turbine combustor section optical image monitoring system that is capable of inspecting, monitoring and/or mapping one or more of visual images, vibration and/or temperature distributions within the combustor section, such as along the length of a combustor transition.

Another need exists for an on-line gas turbine combustor section optical image monitoring system that is externally mounted to a gas turbine combustor without altering the housing structure.

Another need exists for an on-line gas turbine combustor section optical image monitoring system that scans and gathers image information along a substantial length of the combustor section from a single viewing location.

SUMMARY OF THE INVENTION

Accordingly, an object of the invention is to create an on-line gas turbine combustor section optical image monitoring system that is capable of inspecting, monitoring and/or mapping one or more of visual images, vibration and/or temperature distributions within the combustor section, such as along the length of a combustor transition.

Another object of the invention is to create an on-line gas turbine combustor section optical image monitoring system that is externally mounted to a gas turbine combustor without altering the housing structure.

Yet another object of the invention is to create an on-line gas turbine combustor section optical image monitoring system that scans and gathers image information along a substantial length of the combustor section from a single viewing location.

These and other objects are achieved in accordance with the present invention by an on-line operational gas turbine combustion section optical inspection and monitoring system that is externally mounted to existing man way service access within the combustor housing. A replacement man way cover having an optical window is mounted to the combustor housing. One or more optical cameras are oriented so that the camera field of view (FOV) is oriented through the man way cover optical window. The camera FOV is moved to plural positions within the combustion section, such as under control of an automated motion control system, and images are captured. Multiple images are combined to form a composite image, which may include an image of an entire transition within the combustion section. Visual images and/or infrared (IR) thermal images may be captured. Thermal image information may be correlated with actual temperature information obtained from a calibration of the camera using known emissivity paint or other measuring instruments such as field of view (FOV) thermocouples. Composite thermal images of components such as transitions may be created by stitching together images with overlapping field of views. Visual image information may be utilized to determine vibration characteristics of the imaged components, the presence of oxidation and to conduct visual inspection of the components within the field of view.

Embodiments feature a method for on-line optical operational monitoring of an industrial gas turbine combustion section. The method comprises coupling a custom man way cover having an optical window to a combustion section service man way. An optical camera located outside the man way is oriented to look through the optical window, so that it is capable of capturing images of areas of interest within the combustion section. The camera FOV is moved to plural positions within the combustion section and images are captured at each respective position. The captured images are combined in a composite image. The camera FOV may be moved along a length of a combustion section transition between its entrance and exit to form a composite image thereof. Remote temperature monitoring of areas of interest is performed with a calibrated infrared camera. Remote vibration monitoring of areas of interest may also be performed with a spatially calibrated visible camera by monitoring relative motion of the area of interest and correlating the motion with displacement. A fast Fourier transform or discrete Fourier transform may then be used with the known frame rate to determine vibrational frequency. Both infrared and visual cameras may be utilized simultaneously. The cameras may utilize a shared common optical path provided by a beam splitter so that the images from both cameras can be overlaid. Images may be obtained under control of an automated motion and camera control system. The optical monitoring system is desirably retained within a cooling system enclosure.

Another embodiment is directed to an on-line optical operational monitoring system for an industrial gas turbine combustion section, comprising a man way cover having an optical window, adapted for coupling to a combustion section service man way; and an optical camera located outside the man way, having a field of view (FOV) oriented through the optical window, so that the FOV is capable of capturing images of areas of interest within the combustion section. The system also comprises a motion control drive system coupled to the camera for moving the camera FOV to plural positions within the combustion section; and a control system coupled to the motion control system and the camera, for causing the motion control drive system to position the camera and for capturing respective images at each position. An image processing system combines the respective captured images in a composite image.

Yet another embodiment is directed to an on-line optical operational monitoring system for an industrial gas turbine combustion section, comprising a man way cover having an optical window, adapted for coupling to a combustion section service man way. A paired infrared camera and a visible light spectrum camera are coupled to a shared common optical path beam splitter, with both cameras having the same shared field of view (FOV). Both of the cameras are located outside the man way, with the shared FOV oriented through the optical window, so that both cameras are capable of capturing images of the same areas of interest within the combustion section. Respective remote focusing systems are coupled to each camera. Motion control drive systems is coupled to the cameras and beam splitter, for moving the shared camera FOV along translation, roll and tilt motion axes to plural positions within the combustion section. A control system is coupled to the motion control system, the respective remote focusing systems and the respective cameras, for causing the motion control drive system to position the FOV along a selected path and for capturing respective images at each position. An image processing system combines the respective captured images in a composite image that may include temperature information derived from image intensity information captured by the infrared camera and vibration frequency information derived from motion information captured by the visible light spectrum camera. A cooling enclosure outside the man way encloses the camera and motion control systems. A cooling system, such as an air conditioner unit, is coupled to the enclosure for circulating cooling fluid within the enclosure.

The objects and features of the present invention may be applied jointly or severally in any combination or sub-combination by those skilled in the art.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

After considering the following description, those skilled in the art will clearly realize that the teachings of the present invention can be readily utilized in an on-line operational gas turbine combustion section optical inspection and monitoring system that is externally mounted to existing man way service access within the combustor housing, advantageously without modification of the existing combustor housing. A replacement man way cover having an optical window is mounted to the combustor housing. One or more optical cameras are oriented external the combustor housing, so that the camera field of view (FOV) is directed through the man way cover optical window, looking into the combustion section interior. The camera FOV is moved to plural positions within the combustion section, such as under control of an automated motion control system, and images are captured. Multiple images are combined in an image processing system to form a composite image, which may include by way of example an image of an entire transition within the combustion section. Visual images and/or infrared (IR) thermal images may be captured. Thermal image information may be correlated with actual temperature information obtained from other measuring instruments such as thermocouples and composite thermal images of components such as transitions may be created. Image information may be utilized to determine vibration characteristics of the imaged components.

Figure 1:
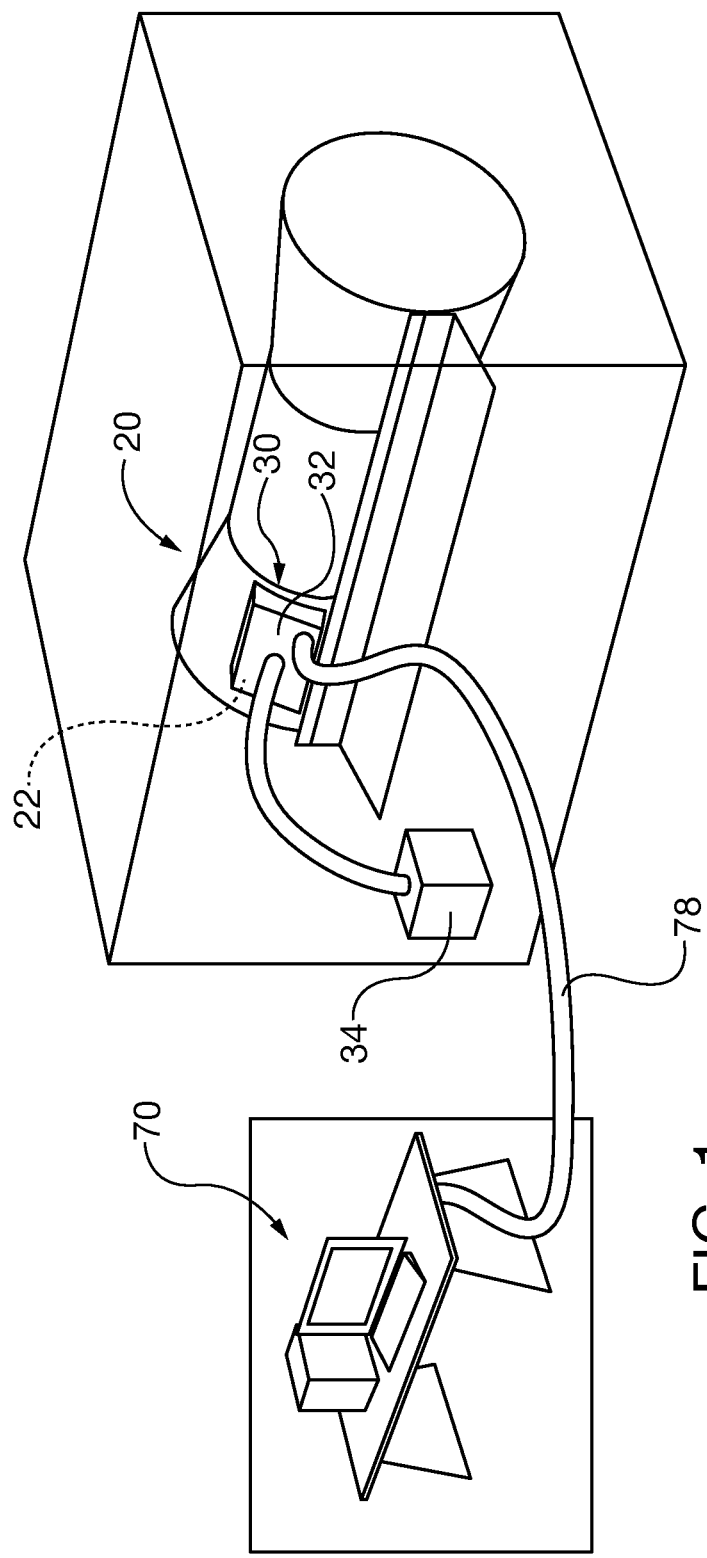
FIG. 1 shows a schematic perspective view of an exemplary on-line optical operational monitoring system of the present invention.
Figure 2:
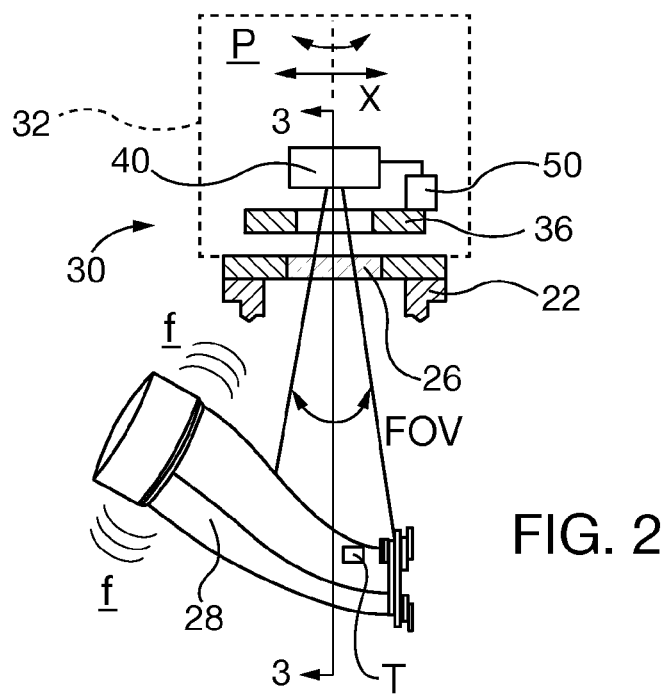
FIG. 2 shows a schematic axial elevational view of the exemplary on-line optical operational monitoring system of FIG. 1 performing an inspection of a combustion turbine transition.
Figure 3:
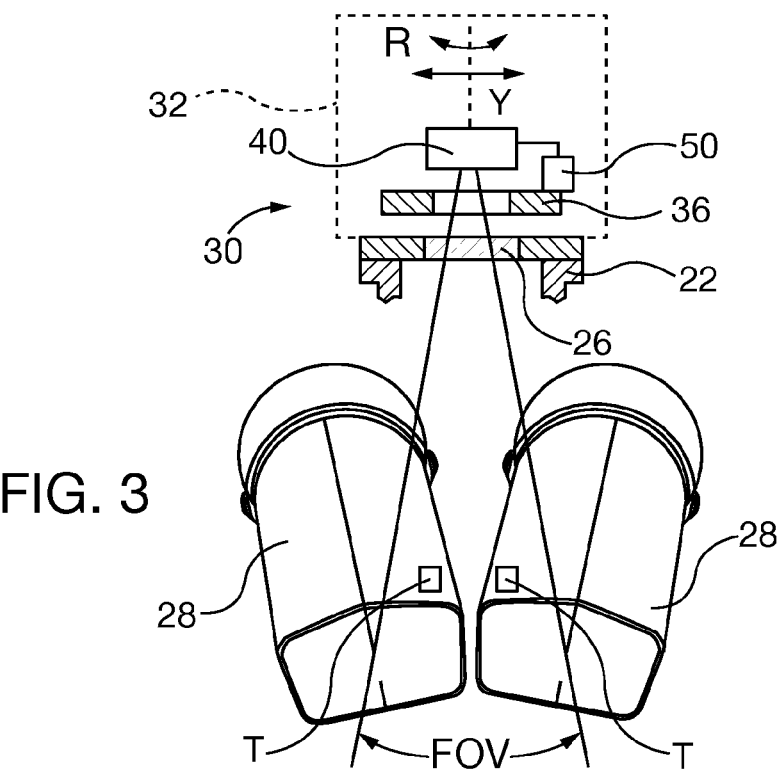
FIG. 3 shows a schematic radial cross-sectional view of the exemplary on-line optical operational monitoring system of FIG. 2 performing an inspection of a combustion turbine transition, taken along 3-3 thereof.

FIGS. 1-3 show an exemplary combustion section casing or housing 20 including a man way 22 service access port. A replacement man way cover 24 is coupled to the man way access port 22 by fasteners (not shown) and includes an optical window 26. The man way cover 24 isolates the combustion section from ambient surroundings. The on-line optical monitoring system 30 preferably includes an external cooling enclosure 32 to isolate the system from the relatively hot ambient environment surrounding the gas turbine combustion section housing 20 and a cooling system 34 that supplies cooling fluid within the enclosure. A suitable cooling system is a portable air conditioning system. An optical camera system 40 containing one or more cameras is oriented relative to the man way cover 24 so that the camera field of view (FOV) is oriented through the man way cover optical window 26. The camera system FOV is moved to plural positions within the combustion section and images are captured at each desired position, preferably under control of an automated motion control system 50. The exemplary motion control system 50 is capable of movement along four axes: translational axes X and Y, pivotal roll R and pivotal pitch P. Other motion axes may be added to or substituted for any of the depicted exemplary axes.

Exemplary combustor transitions 28 are shown in FIGS. 2 and 3. Captured images are processed in an image processing system that can combine respective captured images to form one or more composite images, including composite images of the transition 28. As shown in FIG. 3 two transitions 28 may be scanned and imaged simultaneously through the optical window 26 by selectively translating and pivoting the camera system 40 with the automated motion control system 50. When the gas turbine is operational the transitions 28 are heated by combustion gasses and vibrate at frequency f. A thermocouple T or plurality of thermocouples in an array are affixed to the combustor basket or within the transition 28 (as shown) and respectively provide localized temperature information to the system control station 70 via cable 78.

Figure 4:
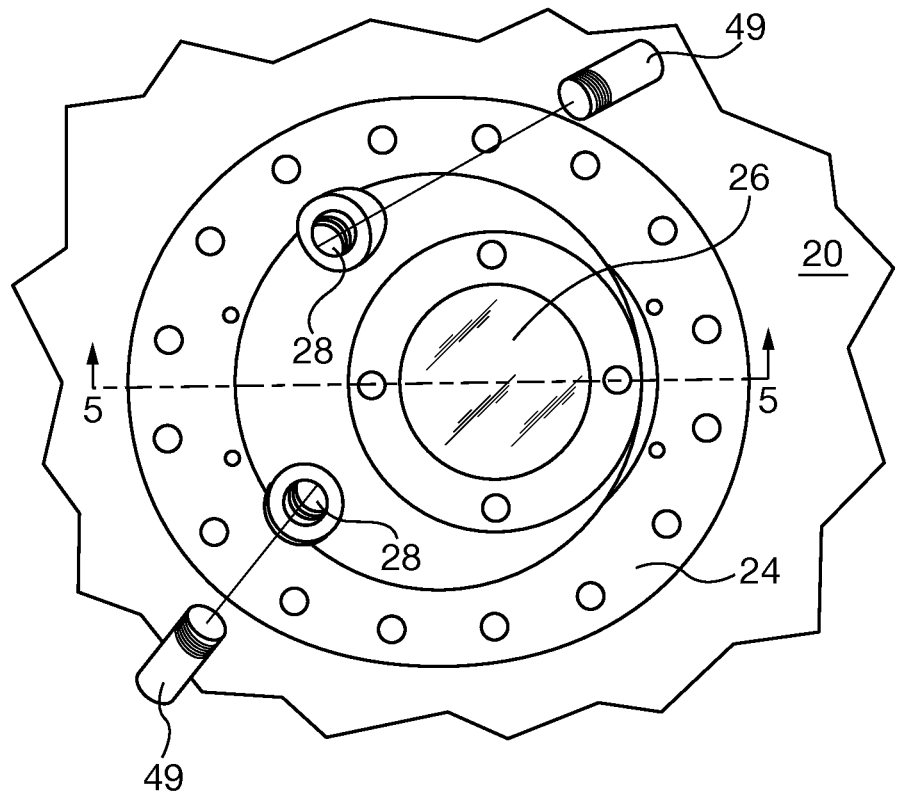
FIG. 4 is a plan view of a man way cover with optical window and illumination ports for use with the on-line optical operational monitoring system of the present invention.
Figure 5:
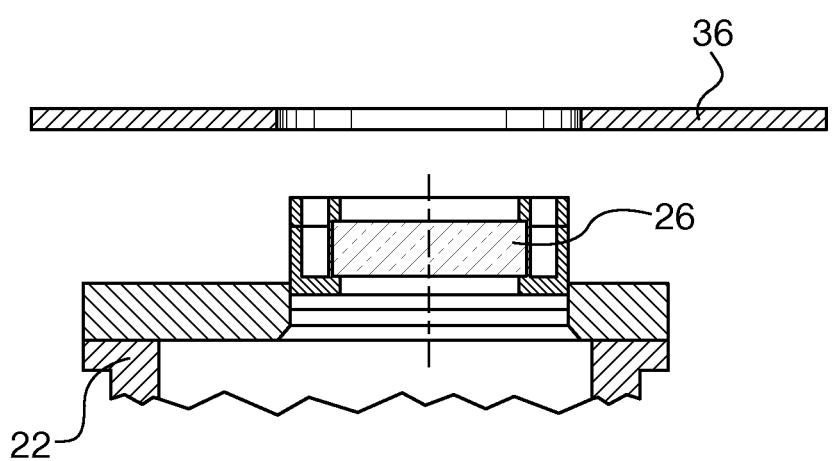
FIG. 5 is an elevational cross-sectional view of the man way cover of FIG. 4, taken along 5-5 thereof.

FIGS. 4 and 5 shows an exemplary man way cover 24 with optical window 26 that is coupled to the man way 22 external flange. The man way cover 24 also has one or more ports 28 for receipt of illumination lamps 49, which are used in conjunction with visual camera inspections. Mounting plate 36 in turn is coupled to the man way cover 24 or any other alternative external mounting structure that facilitates orientation of the optical inspection system 30 field of view through the optical window 26.

Figure 6:
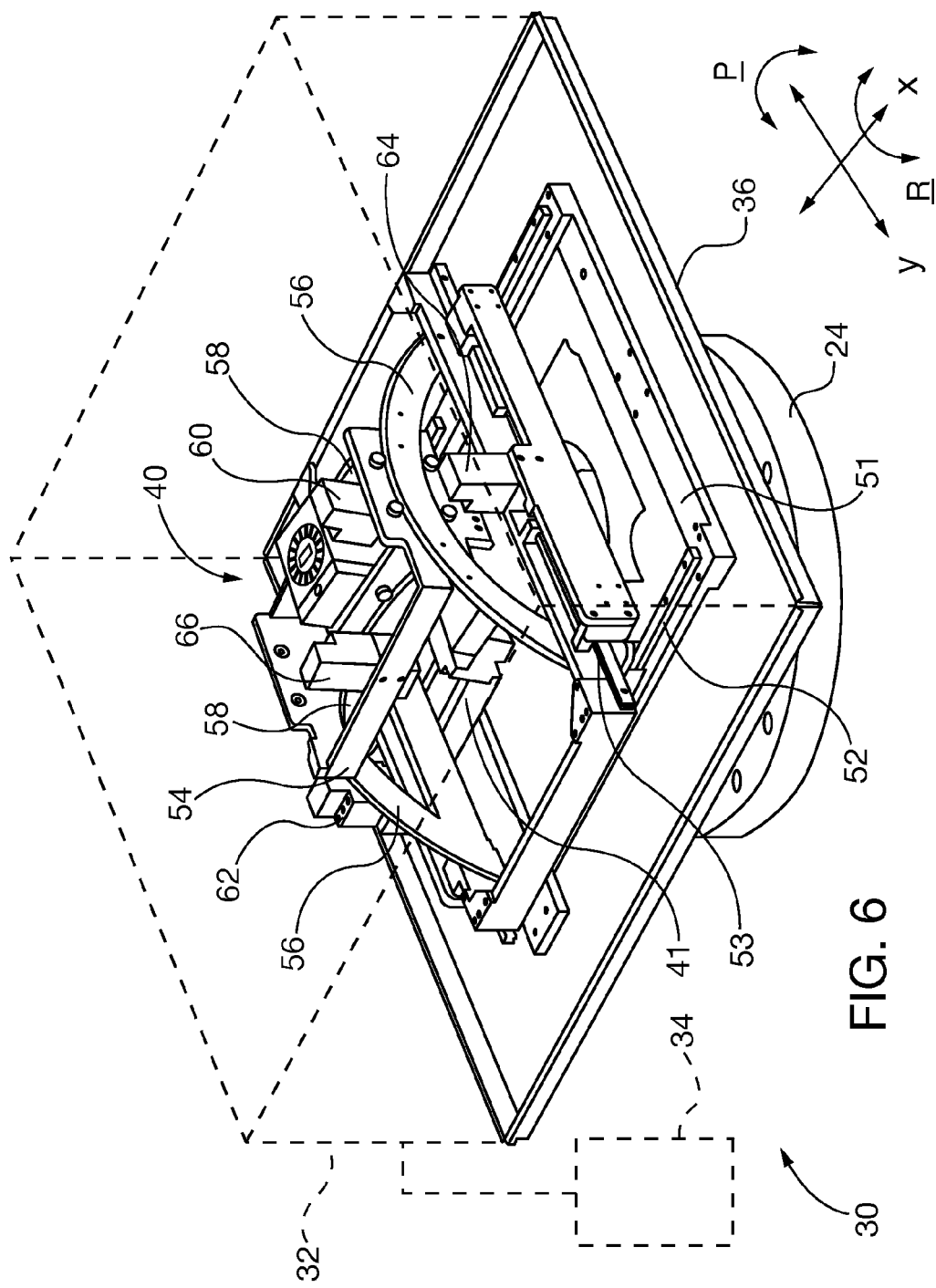
FIG. 6 is a perspective schematic view of an exemplary motion control system used in the on-line optical operational monitoring system of the present invention, with the camera system and cover thereof shown in phantom lines.

The exemplary optical inspection system 30 motion control system 50 is shown in the perspective view of FIG. 6. The monitoring system cover 32 and air conditioning cooling system 34 are shown in phantom. The motion control system a translation table 51 that is coupled to the mounting plate 36. X axis motion carriage 52 facilitates motion along the X axis. Similarly Y axis motion carriage 53 facilitates motion along the Y axis. Camera system frame 54 slidably engages arcuate tracks 56 on rollers, which facilitate pivotal positioning of the camera system FOV along the roll axis R. Pitch arcuate tracks 58 are coupled to the camera system frame 54. Similarly the camera system has a camera mounting base 41 (see also FIG. 7) that slidably engages the pitch arcuate tracks 58 on rollers, which facilitate pivotal positioning of the camera system FOV along the pitch axis P. Other known motion control components and alternative motion axes may be substituted for the exemplary motion control system 50. Respective motion control positioning drives 60, 62, 64 and 66 facilitate selective positioning of the camera system 40 and its field of view along the respective roll (R), X and Y translation, and pitch (P) motion axes.

Figure 7:
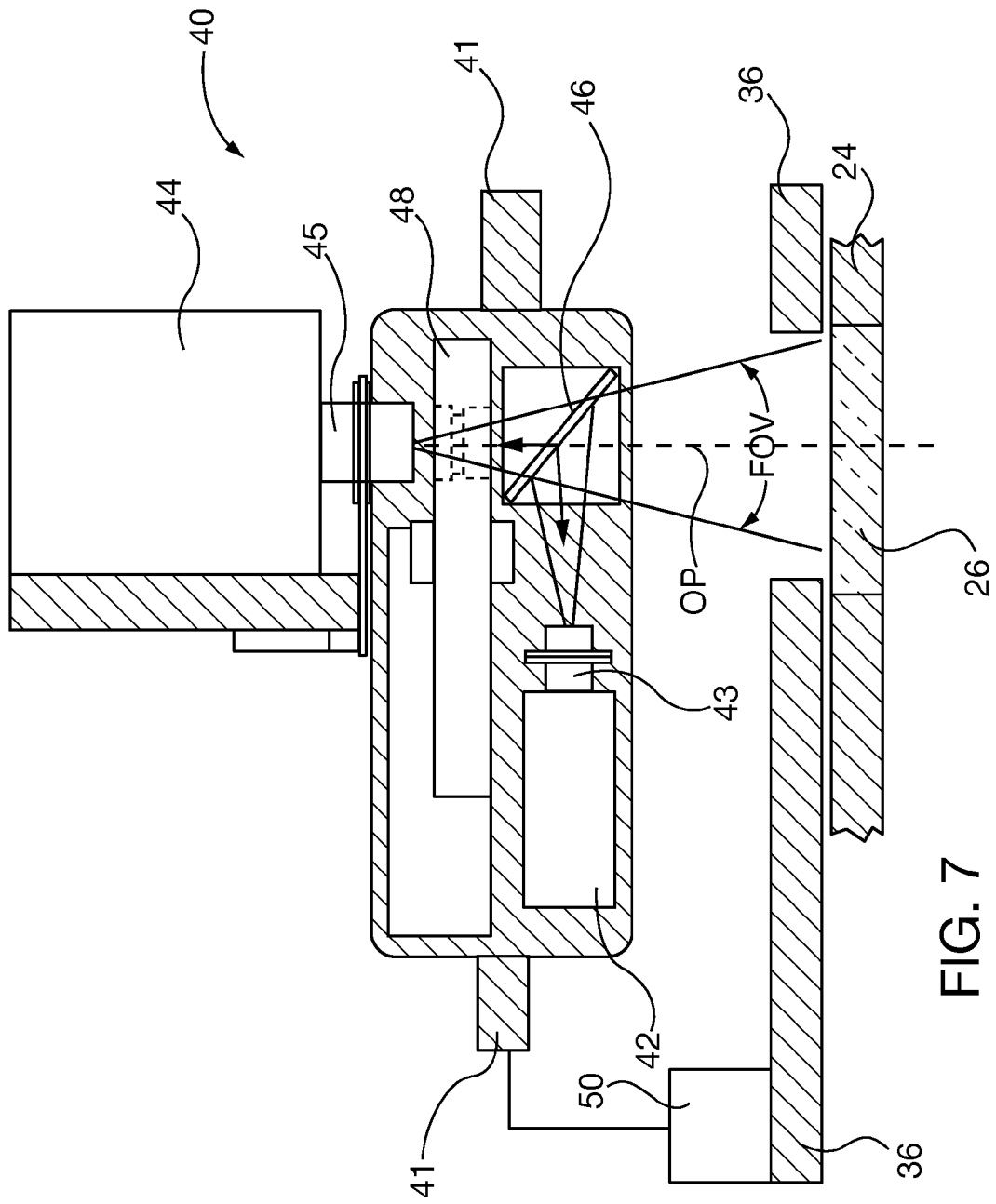
FIG. 7 is an elevational view of an exemplary camera system used with the on-line optical operational monitoring system of the present invention.

An exemplary camera system 40 is shown in FIG. 7. Camera mounting base 41 is coupled to the motion control system 50 for selective orientation of the camera FOV along optical path OP. One or more optical cameras are coupled to the camera mounting base 41 and each may have separate optical paths and fields of view. In this exemplary camera system 40 a pair of a visual light spectrum camera 42 and an infrared IR spectrum camera 44 share a common optical path OP and FOV through optical beam splitter 46, such as a "cold mirror" beam splitter that reflects visible spectrum and transmits infrared spectrum. Each respective camera 42, 44 have a respective remote focusing system 43, 45 shown schematically. Remote focusing may be performed by electromechanical systems or in software with an image processing system. The infrared camera has a neutral density filter 48 comprising a remotely actuated filter wheel to adjust infrared intensity received by that camera.

Figure 8:
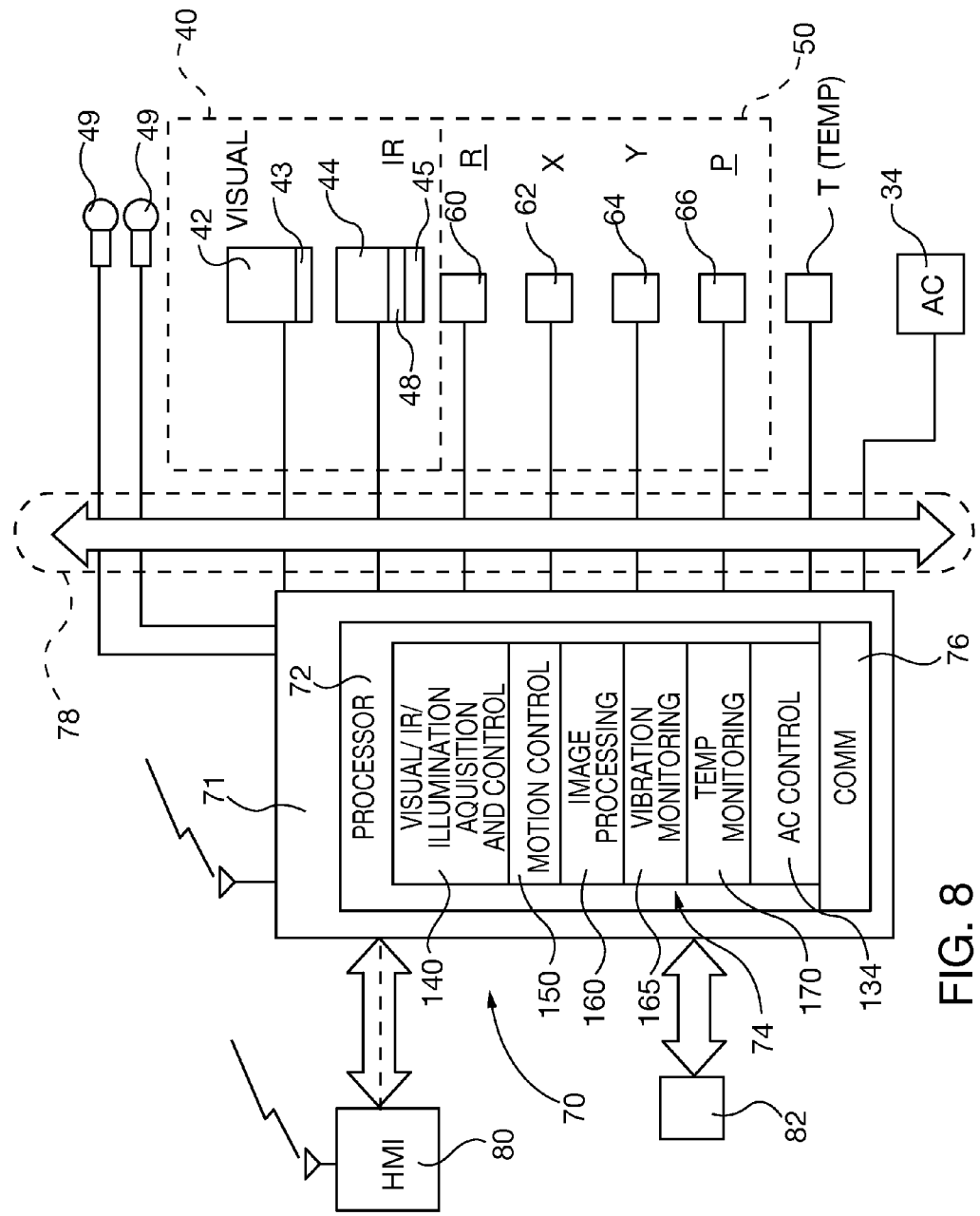
FIG. 8 is a schematic block diagram of an exemplary control system used with the on-line optical operational monitoring system of the present invention.

An exemplary control system for the optical monitoring system 30 is shown in FIG. 8. The control system 70 utilizes a known controller 71 such as an industrial programmable logic controller or personal computer that is in communication with the camera system 40 and motion control system 50. More particularly the controller 71 issues image capture and focus commands to the respective visual and IR cameras/focusing systems 42/43 and 44/45 and receives captured images from them. The controller 71 selectively actuates the IR camera filter wheel to adjust infrared intensity received by the IR camera. It also selectively actuates the illumination lamps 49 when utilizing the visual camera and deactivates the lamps when utilizing the IR camera. The controller 71 also issues motion commands to the motion control system positioning drives 60-66. Additionally the controller 71 receives directly or indirectly operational temperature information from one or more thermocouples T. Optionally the controller 71 may be utilized to control the air conditioning cooling system 34. The controller 71 command and control functions may utilize one or more known feedback loops. The controller 71 communicates with the controlled devices 42, 43, 44, 45, 48, 60-66 and optionally the cooling system 34 or thermocouples T through cable 78, though other types of known communications pathways may be established, including wireless or fiber optic communications.

The controller 71 utilizes a processor 72 and operating system that accesses and implements non-transient instruction software instruction sets stored in an internal or remotely accessible memory 74. Exemplary stored instruction sets selectively incorporate one or more camera image acquisition and control 140 (e.g., image capture, camera focus, IR filter adjustment and/or lamp illumination), motion control 150, image processing 160, vibration monitoring 165, temperature monitoring 170 and air conditioning control 134 functions. The control system 70 is capable of external/remote communication through communications device 76 to one or more human-machine interfaces 80 or remote devices 82 (such as other data processing systems, turbine operational control systems, remote service monitoring systems, data storage devices, etc.). External and remote communications pathways including hard wired single or bi-directional communication, data busses, Internet, Intranet, LAN and wireless communication (e.g., WLAN or WWAN) may be utilized.

It is also to be understood that the present invention control system 70 may be implemented in various forms of hardware, software, firmware, special purpose processors, or a combination thereof. As described above, preferably the present invention is implemented in software as one or more program instruction sets tangibly embodied on a program storage device. The program(s) may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may be either part of the microinstruction code or part of the program (or combination thereof) which is executed via the operating system. In addition, various other peripheral devices may be connected to the computer platform such as additional data storage devices, other remote information processing systems and human machine interfaces.

It is also to be understood that, because some of the constituent system components and method steps depicted in the accompanying figures are preferably implemented in software, the actual connections between the system components (or the process steps) may differ depending upon the manner in which the present invention is programmed. Specifically, any of the computers or devices may be interconnected using any existing or later-discovered networking technology and may also all be connected through a lager network system, such as a corporate network, metropolitan network or a global network, such as the Internet.

Image processing may be performed directly within the control system 70 or by a separate image processing system that is coupled to the control system. In an exemplary imaging scan of one or more combustion section transitions 28 shown in FIGS. 2-3, the control system 70 causes the motion control system to position the camera system 40 FOV along the length of one or two adjacent transitions. During the scan the control system 70 causes the camera system 40 to vary focus as necessary for image quality and to capture image snapshots along the transition 28 length and the images may be stored for future analysis. Adjacent images are stitched into a composite image using known image processing software. Thermal IR composite images map temperature variations along the transition length based on relative change in IR intensity. The intensity variations are correlated with actual temperatures by comparing the IR intensities with blackbody intensities/temperature data stored in the control system 70 or in a separate image processing system. Blackbody data derived temperature is calibrated with actual temperature measured by a thermocouple T within or proximal to the scan FOV or by emissivity calibration by viewing paint or other objects having a known emissivity that is placed within the field of view, and thereafter adjusting the other derived temperatures. Visual images enable operators to inspect transitions for structural defects. Transition vibration frequency f can be determined by correlating variations in position of a reference marker on the transition outer surface taken at different image sample times. Position variations between sample scans are attributed to varying orientations between the camera and outer surface caused by transition vibratory motion. Vibrational variations can be mapped along the length of the transition 28.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

What is claimed is:

1. A method for on-line optical operational monitoring of an industrial gas turbine combustion section, comprising:
    coupling a man way cover having an optical window to a combustion section service man way;
    directing the field of view (FOV) of an optical camera located outside the man way cover through the optical window, so that the FOV is capable of capturing images of areas of interest within the combustion section;
    moving the camera FOV to plural positions within the combustion section and capturing respective images at each position; and
    combining the respective captured images in a composite image
    remote vibration monitoring of the areas of interest by monitoring relative motion of the areas of interest and correlating the motion with vibrational frequency.

2. The method of claim 1, comprising moving the camera FOV along a length of a combustion section transition between its entrance and exit to form a composite image thereof.

3. The method of claim 1, further comprising remote monitoring temperature of areas of interest within an infrared camera FOV by correlating captured image infrared intensity with temperature.

4. The method of claim 3, the correlating step performed by comparing captured FOV image intensity with blackbody intensity calibration data and fine tuning the calibration data with independently obtained temperature information that is relevant to the area of interest within the FOV.

5. The method of claim 4, the calibrating step performed by obtaining temperature information from a thermocouple or known emissivity object within the combustion section.

6. The method of claim 1, further comprising remote monitoring visual images of areas of interest within a visible light spectrum camera FOV.

7. The method of claim 1 further comprising simultaneous monitoring of the FOV with an infrared camera and a visible light spectrum camera coupled to a shared common optical path beam splitter.

8. The method of claim 1, the orienting FOV step performed with an automated motion control system coupled to the optical camera that automatically positions the camera and captures images along a selected path within the combustion section.

9. The method of claim 8, comprising automatically positioning the camera FOV along a length of a combustion section transition between its entrance and exit with the automated motion control system and capturing images to form a composite image thereof.

10. The method of claim 1 comprising cooling the camera and associated monitoring system components by isolating them within an enclosure outside the man way and circulating cooling fluid within the enclosure.

11. An on-line optical operational monitoring system for an industrial gas turbine combustion section, comprising:
a man way cover having an optical window, adapted for coupling to a combustion section service man way;
an optical camera located outside the man way cover, having a field of view (FOV) directed through the optical window, so that the FOV is capable of capturing images of areas of interest within the combustion section;
a motion control drive system coupled to the camera for moving the camera FOV to plural positions within the combustion section;
a control system coupled to the motion control system and the camera, for causing the motion control drive system to position the camera and for capturing respective images at each position; and
an image processing system for combining the respective captured images in a composite image
a remote vibration monitoring system correlating a motion of the areas of interest with vibrational frequency.

12. The system of claim 11, comprising an infrared camera capable of capturing FOV image intensity and the image processing system capable of correlating captured image intensity with temperature.

13. The system of claim 12, the correlation performed by the image processing system comparing captured FOV image intensity with blackbody intensity emission/temperature calibration and adjusting the calibration with temperature information obtained from a thermocouple or known emissivity object within the camera FOV.

14. The system of claim 11, comprising a visible light spectrum camera for capturing visible images.

15. The system of claim 11, comprising an infrared camera and a visible light spectrum camera coupled to a shared common optical path beam splitter, with both cameras having the same shared FOV.

16. The system of claim 15, cameras having respective remote focusing systems coupled to the control system.

17. The system of claim 16, the motion control drive system comprising camera FOV translation, roll and tilt motion axes.

18. The system of claim 11, the control system automatically positioning the camera FOV along a selected path with the motion control system and capturing images to form a composite image.

19. The system of claim 18, the control system automatically positioning the camera FOV along a length of a combustion section transition between its entrance and exit with the automated motion control system and capturing images to form a composite image thereof.

20. The system of claim 11, further comprising a cooling enclosure outside the man way enclosing the camera and motion control system, and a cooling system coupled to the enclosure, for circulating cooling fluid within the enclosure.

21. An on-line optical operational monitoring system for an industrial gas turbine combustion section, comprising:
a man way cover having an optical window, adapted for coupling to a combustion section service man way;
a paired infrared camera and a visible light spectrum camera coupled to a shared common optical path beam splitter, with both cameras having the same shared field of view (FOV), the cameras located outside the man way cover, with the shared FOV directed through the optical window, so that the FOV is capable of capturing images of areas of interest within the combustion section;
respective remote focusing systems coupled to each camera;
a motion control drive system coupled to the cameras and beam splitter, for moving the camera FOV along translation, roll and tilt motion axes to plural positions within the combustion section;
a control system coupled to the motion control system the respective remote focusing systems and the respective cameras, for causing the motion control drive system to position the FOV along a selected path and for capturing respective images at each position;
an image processing system for combining the respective captured images in a composite image that may include temperature information derived from image intensity information captured by the infrared camera and vibration frequency information derived from motion information captured by the visible light spectrum camera; and
a cooling enclosure outside the man way enclosing the camera and motion control system, and a cooling system coupled to the enclosure, for circulating cooling fluid within the enclosure.

* * * * *